DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED NOVEMBER 24, 1970

880 O.G. 1162

T880,005

PROCESS FOR MANUFACTURING 2,2,4-TRIMETHYLPENTANOL

Hugh J. Hagemeyer, Jr., David C. Hull, and Milton A. Perry, Longview, Tex., assignors to Eastman Kodak Company, Rochester, N.Y., a corporation of New Jersey

Continuation of application Ser. No. 786,458, Dec. 23, 1968, which is a continuation-in-part of application Ser. No. 379,009, June 29, 1964. This application Dec. 22, 1969, Ser. No. 883,663

Int. Cl. C07c *31/02*

U.S. Cl. 260—638

No Drawing. 7 Pages Specification

A process for the manufacture of 2,2,4-trimethylpentanol which comprises contacting an ester of 2,2,4-trimethyl-3-pentenol having the formula

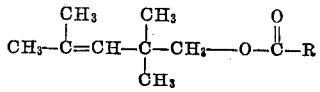

wherein R is alkyl of 1 to 17 carbon atoms, phenyl, o-, m- or p-tolyl, benzylyl or cyclohexyl; with hydrogen at a temperature from about 185° C. to about 275° C. and a pressure in the range of about 2000 p.s.i. to about 10,000 p.s.i. over a copper-chromium oxide catalyst.